: US008893925B2

(12) United States Patent
Cheetham

(10) Patent No.: US 8,893,925 B2
(45) Date of Patent: *Nov. 25, 2014

(54) MIXING AND DISPENSING CONTAINER

(75) Inventor: Joshua James Cheetham, Chicago, IL (US)

(73) Assignee: SDI (North America), Inc., Bensenville, Chicago, IL (US)

( * ) Notice: Subject to any disclaimer, the term of this patent is extended or adjusted under 35 U.S.C. 154(b) by 445 days.

This patent is subject to a terminal disclaimer.

(21) Appl. No.: 12/873,064

(22) Filed: Aug. 31, 2010

(65) Prior Publication Data

US 2011/0056984 A1 Mar. 10, 2011

(30) Foreign Application Priority Data

Sep. 8, 2009 (AU) ................................. 2009904280

(51) Int. Cl.
*B67D 7/60* (2010.01)
*A61C 5/04* (2006.01)
*A61C 5/06* (2006.01)

(52) U.S. Cl.
CPC .................. *A61C 5/066* (2013.01); *A61C 5/064* (2013.01)
USPC ...................... 222/145.5; 222/541.3; 222/386; 433/90

(58) Field of Classification Search
USPC ............. 222/145.1, 145.5, 541.3, 541.1, 386, 222/326–327, 136; 433/90
See application file for complete search history.

(56) References Cited

U.S. PATENT DOCUMENTS

| 3,684,136 | A | * | 8/1972 | Baumann | 222/386 |
| 3,727,802 | A | * | 4/1973 | Schnurmacher | 222/205 |
| 3,739,947 | A | * | 6/1973 | Baumann et al. | 222/136 |
| 4,030,643 | A | * | 6/1977 | van Manen | 222/386 |
| 4,648,532 | A | * | 3/1987 | Green | 222/82 |
| 4,941,751 | A | * | 7/1990 | Muhlbauer | 366/182.1 |
| 5,026,283 | A | * | 6/1991 | Osanai et al. | 433/90 |
| RE33,801 | E | * | 1/1992 | Green | 222/82 |
| 5,154,321 | A | * | 10/1992 | Shomer | 222/129 |
| 5,172,807 | A | * | 12/1992 | Dragan et al. | 206/219 |
| 5,284,275 | A | * | 2/1994 | Shomer | 222/145.6 |
| 5,392,904 | A | * | 2/1995 | Frick et al. | 206/219 |
| 5,871,355 | A | * | 2/1999 | Dragan et al. | 433/90 |
| 6,386,872 | B1 | * | 5/2002 | Mukasa et al. | 433/90 |
| 6,543,611 | B1 | * | 4/2003 | Peuker et al. | 206/219 |
| 6,682,347 | B2 | * | 1/2004 | Aoyagi et al. | 433/90 |
| 6,715,645 | B2 | * | 4/2004 | Peuker et al. | 222/129 |
| 6,776,516 | B2 | * | 8/2004 | Suzuki et al. | 366/139 |
| 6,821,012 | B2 | * | 11/2004 | Suzuki et al. | 366/139 |
| 6,869,284 | B2 | * | 3/2005 | Aoyagi et al. | 433/90 |
| 8,074,794 | B2 | * | 12/2011 | Nakatsuka et al. | 206/222 |
| 8,177,102 | B2 | * | 5/2012 | Hammond et al. | 222/391 |
| 8,584,838 | B2 | * | 11/2013 | Cheetham | 206/219 |

(Continued)

*Primary Examiner* — Patrick M Buechner
(74) *Attorney, Agent, or Firm* — William H. Holt

(57) ABSTRACT

A container (10) for mixing and dispensing material includes a body (12) having a main chamber (17), a dispensing nozzle (26), a liquid receptacle (16) and a plunger (18). The liquid receptacle (16) has a front portion arranged to break away upon pressure being applied by the plunger (18) so that the plunger (18) can traverse the entire length of the body (12). This enables a charge of material in the main chamber (17) to be entirely dispensed through a frangible wall (22) into the nozzle (26). The container (10) is particularly envisaged for use in mixing and dispensing of dental material.

7 Claims, 8 Drawing Sheets

(56) References Cited

U.S. PATENT DOCUMENTS

| | | | |
|---|---|---|---|
| 2001/0053511 A1* | 12/2001 | Aoyagi et al. | 433/90 |
| 2002/0098462 A1* | 7/2002 | Kaneko et al. | 433/89 |
| 2004/0011815 A1* | 1/2004 | Martin | 222/136 |
| 2004/0020796 A1* | 2/2004 | Cheetham et al. | 206/63.5 |
| 2011/0056853 A1* | 3/2011 | Cheetham | 206/219 |
| 2011/0056984 A1* | 3/2011 | Cheetham | 222/135 |
| 2012/0295221 A1* | 11/2012 | Cheetham | 433/90 |
| 2014/0034670 A1* | 2/2014 | Cheetham | 222/82 |

* cited by examiner

MIXING AND DISPENSING CONTAINER

FIELD OF THE INVENTION

The present invention relates to a mixing and dispensing container.

SUMMARY OF THE INVENTION

In accordance with one aspect of the present invention there is provided a container for the mixing and dispensing of material, which comprises a body having a main chamber, a dispensing nozzle, a liquid receptacle and a plunger, wherein the plunger is in engagement with the liquid receptacle such that, in use, upon the plunger being depressed liquid in the receptacle is pushed from the receptacle into the main chamber of the body so as to contact material in the main chamber, wherein subsequently a front portion of the liquid receptacle is arranged to be broken away by depression of the plunger such that the plunger is able to traverse the entire length of the main chamber to facilitate dispensation of material into the dispensing nozzle.

DESCRIPTION OF THE DRAWINGS

The present invention will now be described, by way of example, with reference to the accompanying drawings, in which:

FIG. 3b is a longitudinal sectional view of the container of FIG. 1 showing an alternative embodiment to that of FIG. 3a;

FIG. 4 is a longitudinal sectional view of the container of FIG. 1 in a fully activated condition of the embodiment shown in FIG. 3a;

DETAILED DESCRIPTION OF THE DRAWINGS

Referring to the FIGS. 1 to 4, there is shown a container that is particularly envisaged to be used for dispensing of a dental material, in which a front part of a liquid receptacle breaks away from the liquid receptacle.

Figure 1:
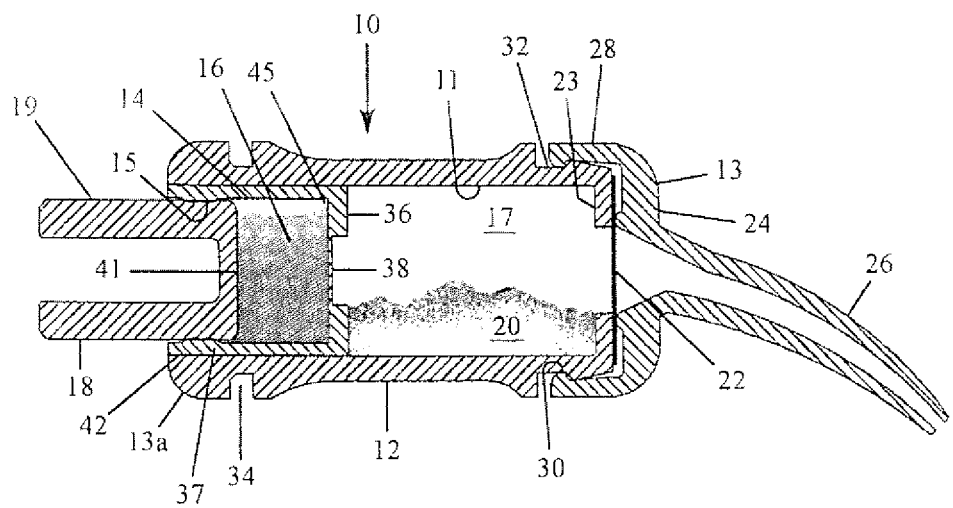
FIG. 1 is a longitudinal sectional view of a container in accordance with the present invention in an initial condition.
Figure 5:
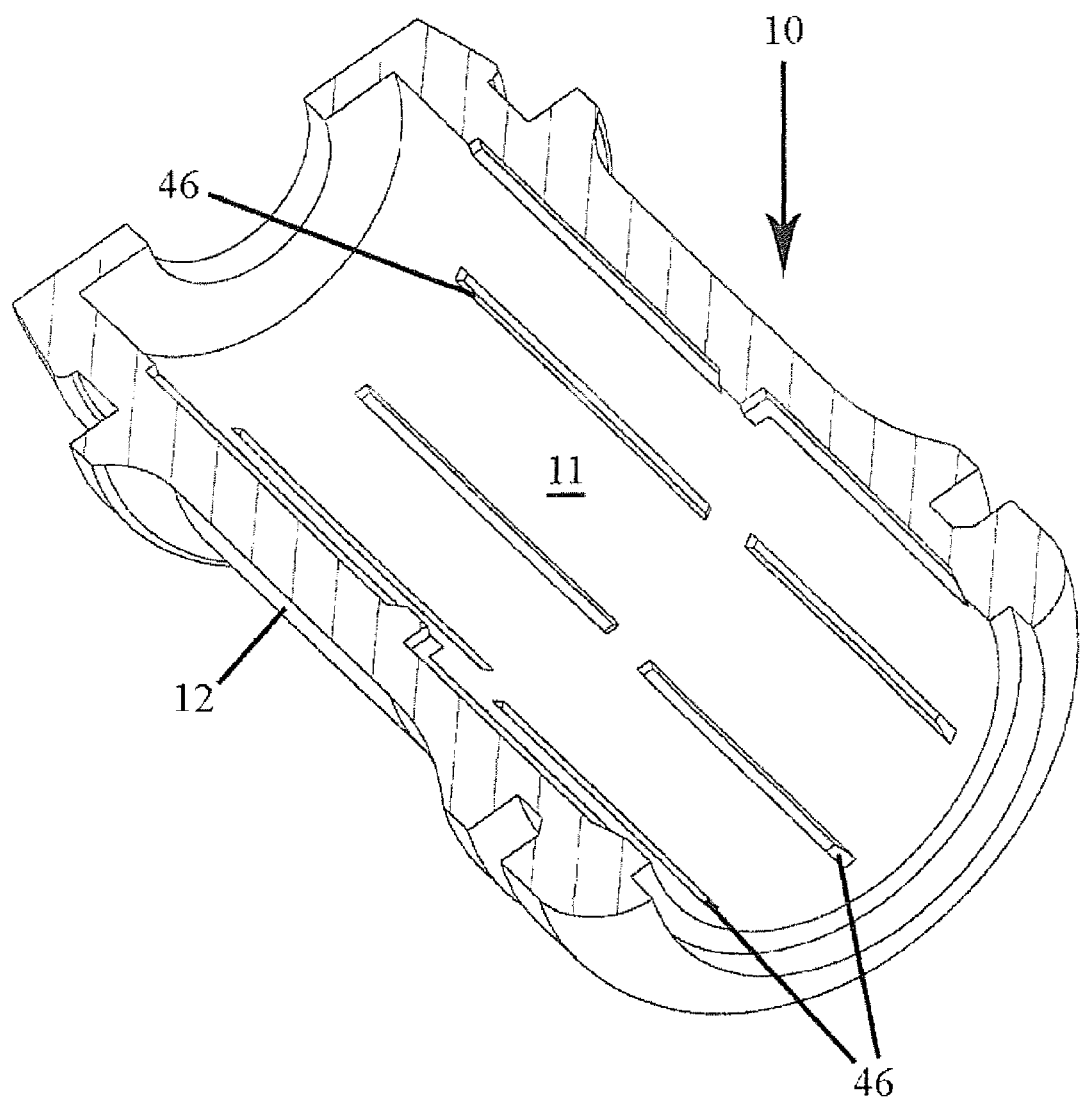
FIG. 5 is a longitudinal sectional perspective view of a body of the container of FIGS. 1 to 4 showing vent means formed to therein.
Figure 6:
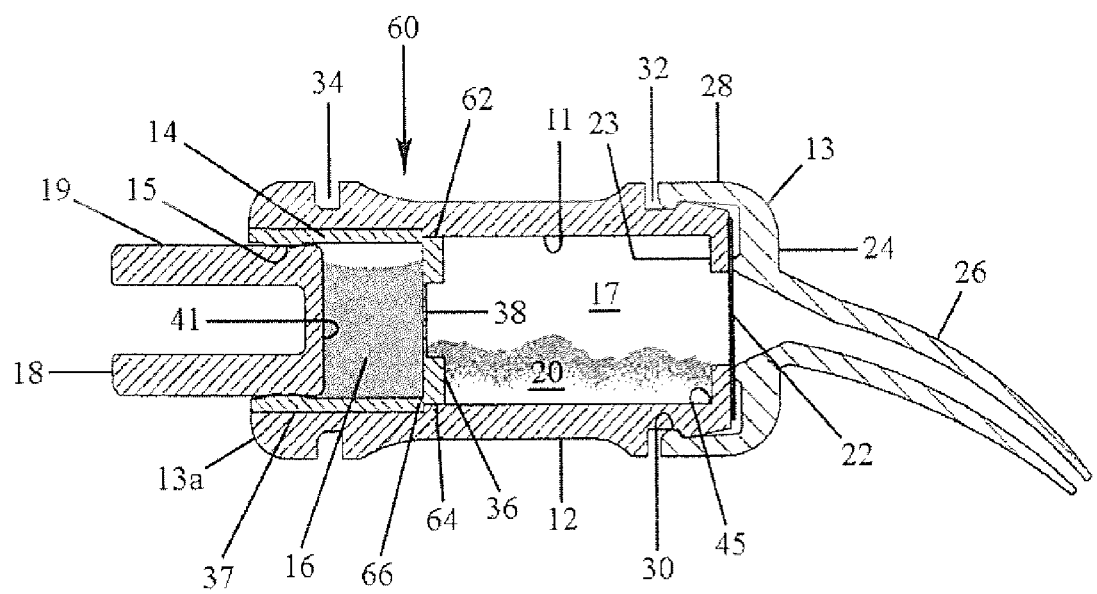
FIG. 6 is a longitudinal section of a container in accordance with a further embodiment of the present invention in an initial condition.
Figure 7:
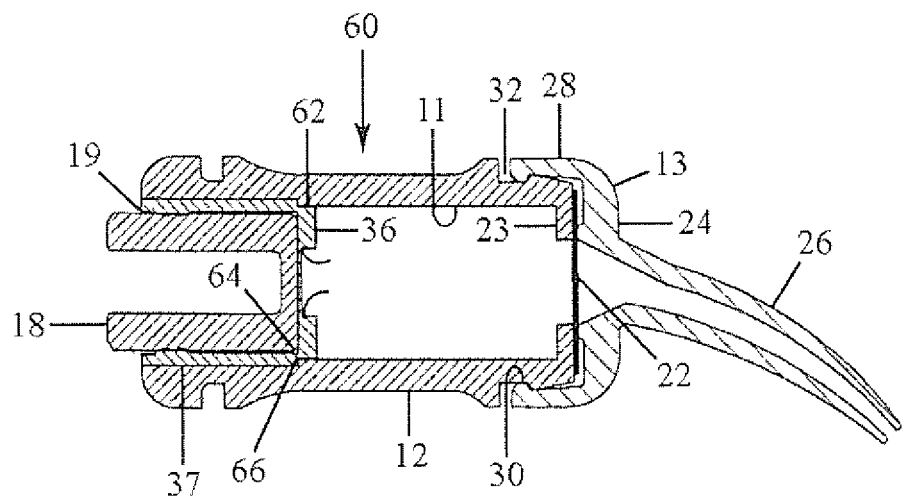
FIG. 7 is a longitudinal section of the container of FIG. 6 in a particularly activated condition.

Referring to FIG. 1, there is shown a container 10 in an initial open or storage condition. The dental container 10 comprises a body 12 which has an internal surface 11 and is substantially cylindrical in cross section. Inside the body 12 is an open ended liquid receptacle 14, which contains a liquid 16. The receptacle 14 is sealed by a plunger 18 such as by seal means (FIG. 5) located on an external surface 19 of the plunger 18 or on an internal surface 15 of the liquid receptacle 14. The plunger 18 is located in an open end of the receptacle 14 as shown and has a front face 41

The body 12 contains a main chamber 17 which is arranged to house an amount of powder 20. The body 12 is sealed at a distal end 13 by a frangible membrane 22 which is connected to the body 12 such as at an annular inwardly extending flange 23 by any convenient means such as an adhesive. The distal end 13 of the body 12 is opposed to a proximal end 13a thereof. The body 12 has attached thereto an end cap 24 which is connected to a nozzle 26 for dispensing material. The cap 24 is connected to the body 12 by means of a circumferential flange 28 which has an inwardly extending annular rib 30 at an end thereof remote from the nozzle 26. The rib 30 engages with a circumferential recess 32 in the body 12.

Figure 1A:
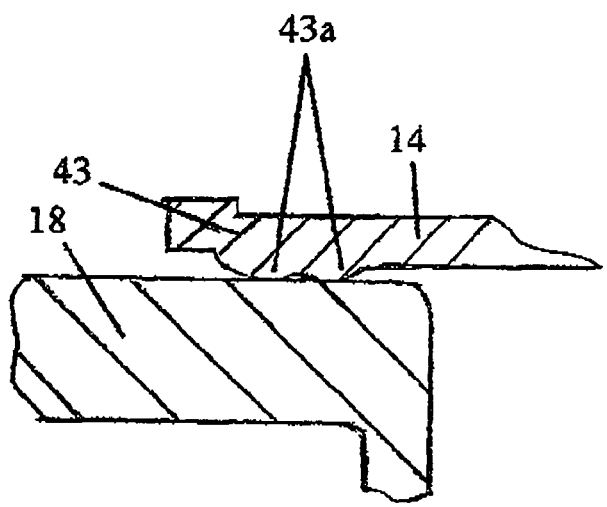
FIG. 1a is a partial sectional view of the container of FIG. 1 to an enlarged scale showing a seal arrangement.

As shown in FIG. 1a, there is preferably provided a liquid tight seal 43 between the receptacle 14 and of the plunger 18. The seal 43 comprises annular ribs 43a which extend outwardly from the receptacle 14 to the plunger 18 or vice versa.

Further, the body 12 is provided with an outward facing circumferential groove 34 adjacent the plunger 18. The groove 34 is arranged to engage with a dispensing apparatus (not shown) in use.

Still further, the liquid receptacle 14 has a side wall 37 and an inner wall 36 with a central weakened portion 38. The central weakened portion 38 is substantially thinner than the inner wall 36 of the liquid receptacle 14. A junction between the side wall 37 and the inner wall 36 is defined by an angle 45. The inner wall 36 is, in the condition shown in FIG. 1, spaced from a front face 41 of the plunger 18.

Figure 2:
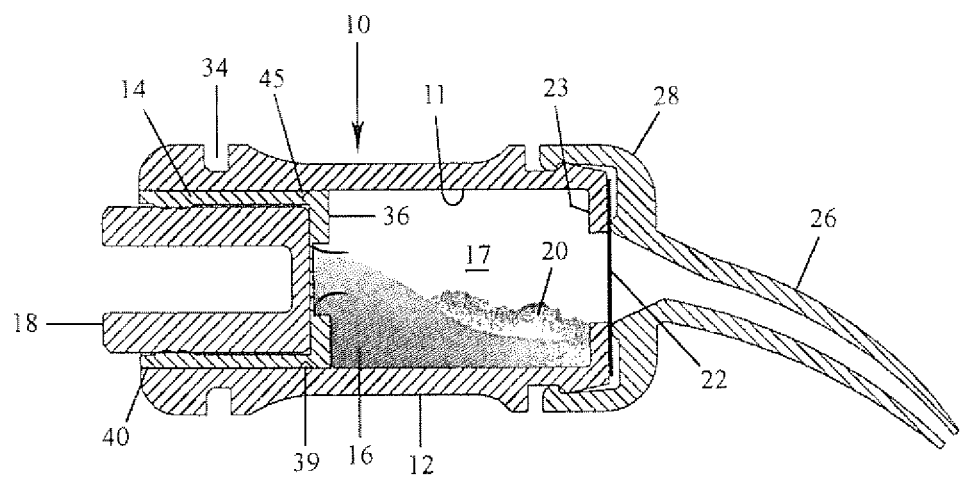
FIG. 2 is a longitudinal sectional view of the container of FIG. 1 in a partially activated condition.

Referring to FIG. 2, there is shown the container 10 in an activated position. The activated position is achieved though the plunger 18 being depressed. This action causes the plunger 18 to be moved so that an inner end thereof contacts the inner wall 36. This displaces the liquid 16 so that the weakened portion 38 of the inner wall 36 breaks due to the hydraulic pressure applied to it by the liquid 16. The liquid 16 is then forced into the main chamber 17 of the body 12. The container 10 may then placed into a known vibrating mixing device. The liquid 16 and the powder 20 are admixed and thereby form a paste in the chamber 17.

Figure 3A:
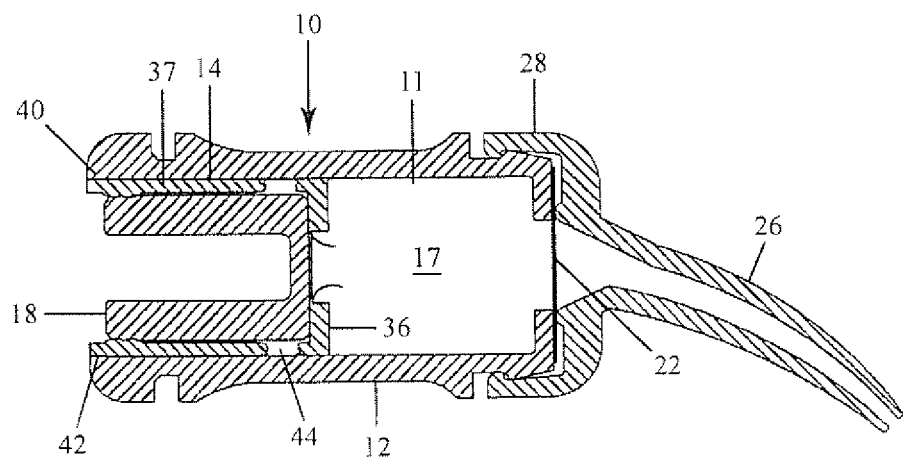
FIG. 3a is a longitudinal sectional view of the container of FIG. 1 in a further partially activated condition.

Referring to FIG. 3a, there is shown the container 10 after the plunger 18 has been depressed and the liquid 16 and the powder 20 have been mixed to form a paste. The main chamber 17 of the body 12 now contains the paste. A front part of the liquid receptacle 14 including the inner wall 36 and part of a side wall 37 thereof have broken away from the remainder of the liquid receptacle 14. This is caused by force being transferred from the plunger 18 to the front part of the liquid receptacle 14 during dispensing of the paste with a dispensing apparatus. The remainder of the liquid receptacle 14 remains in place by virtue of an outwardly projecting annular step 40 on the liquid receptacle 14 engaging with an annular recess 42 in the inner surface 11 of the body 12. In this embodiment of the present invention the side wall 37 is preferably provided with a weakened region 39 at the desired break point such as by the side wall 37 being made thinner at this point (see FIG. 2).

Figure 3B:
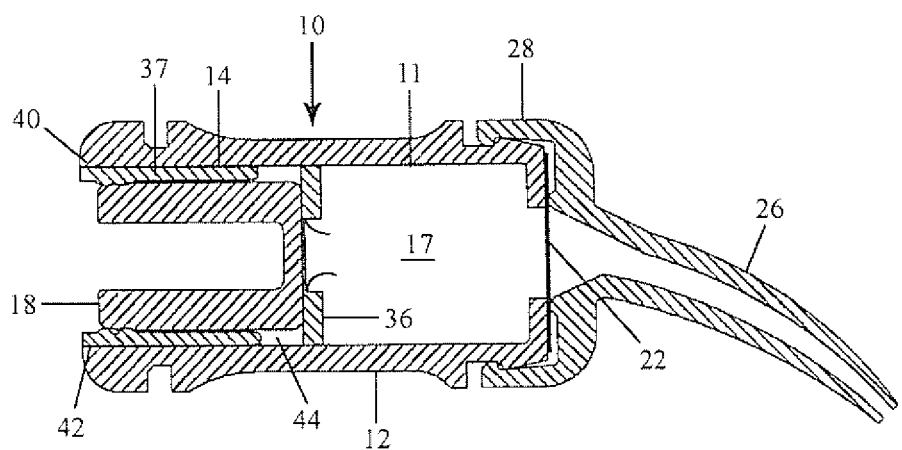

Referring to FIG. 3b, there is shown the container 10 after the plunger 18 has been depressed and the liquid 16 and the powder 20 have been mixed to form a paste. In this embodiment a front part of the liquid receptacle 14, including the inner wall 36 has broken away from the remainder of the receptacle 14 in a manner that leaves the side wall 37 substantially intact. This is caused by force being transferred from the plunger 18 to the front part of the liquid receptacle 14 during dispensing. The remainder of the liquid receptacle remains in place by virtue of an outwardly extending annular step 40 engaging on the liquid receptacle 14 with an annular recess 42 on the inner wall 11 of the body 12. As shown in FIG. 3b there is preferably a sharp substantially right angle bend 45 between the inner wall 36 and the side wall 37 of receptacle 14. The bend 45 is preferably devoid of any radius and provides a stress concentration point to facilitate breaking off of the inner wall 36. Force placed on the plunger 18 tends to cause a transfer and concentration of energy at the bend 45 leading to separation of the inner wall 36 at the bend 45 as shown in FIG. 3b.

Figure 4:
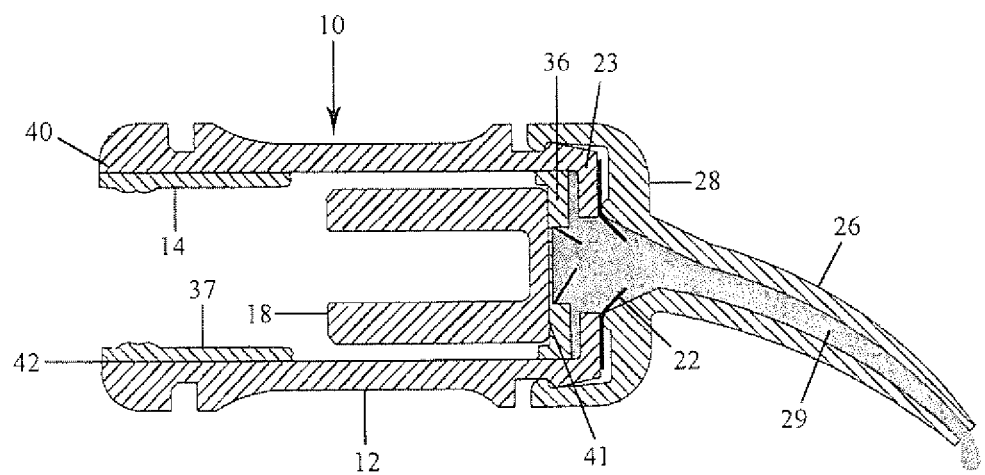

As shown in FIG. 4, the plunger 18 forces the front of the liquid receptacle 14 along the main chamber 17, where the front part of the liquid receptacle 14 acts as a seal and prevents paste 28 from travelling rearwardly. Means such as slots located in the main body internal wall 11 may be provided to act as vent means for entrapped air to escape from the powder 20. The entrapped air will vent into a recess 44 created from the separation of the front part of the liquid receptacle 14. (See FIGS. 3a and 3b). The slots may take the form of a plurality of elongated substantially parallel slots 46 which can be seen in FIG. 5, or other forms Referring to FIG. 4, there is shown the container 10 once substantially all of the paste has been dispensed. The front part of the liquid receptacle 14 has been displaced forward by the plunger 18 until it approaches the flange 23 of the body 12. As the plunger 18 is displaced forwardly hydraulic pressure on the paste bursts the membrane 22, allowing fluid communication between the main chamber 17 and the nozzle 26 and subsequent dispensing of the paste to the desired location.

In use, a user places the container 10 into an appropriate dispensing device (not shown) by any convenient means 34 to allow for the application of pressure to the plunger 18. Pressure applied to the plunger 18 builds hydraulic pressure against the weakened portion 38 through displacement of the liquid 16. Once the hydraulic pressure reaches a critical point the weakened portion 38 breaks and the liquid 16 then enters the main chamber 17. The plunger 18 is then displaced forward again by the dispensing device. This brings the front face 41 of the plunger 18 into close abutting contact with a rear face of the inner wall 36.

The main chamber 17 now contains the liquid 16 and the powder 20. The user then places the dental applicator in an appropriate mixing device such as a vibration mixer. The agitation caused by the mixing device causes the liquid 16 and the powder 20 to mix and combine to form a paste 29 (See FIG. 4).

After mixing, further forward displacement of the plunger 18 places increasing pressure against the liquid receptacle 14. Once sufficient force is applied the front section of the liquid receptacle 14 breaks away as shown in FIGS. 3a and 3b. This leaves the side wall 37 of the liquid receptacle 14 substantially intact.

As the plunger 18 is displaced forward slots in the interior surface 11 of the main chamber 17 may allow for any air trapped within the container or mixed material to vent into a recess 44 created from the separation of the front part of the liquid receptacle 14 from the side wall 37. Further, it is possible that the mixing process does not fully mix all of the powder 20 components and some residual powder is left behind in, for example, the area between the front part of the liquid receptacle 14 and the internal wall 11 of the body 12. This in practice may cause issues with the area being treated by the dental material becoming contaminated by residual powder component. As the plunger 18 and inner wall 36 move forward the recess 44 is formed behind the inner wall 36. Powder particles that have remained unmixed are able to escape around the front part and into the recess, hence reducing the risk of contamination or exposure of the user of these particles.

Further forward displacement of the plunger 18 will cause the plunger 18 to travel to the distal end of the body 12 as shown in FIG. 4. This will lead to increased hydraulic pressure against the frangible membrane 22. Once the hydraulic pressure reaches a critical value the membrane 22 will burst. The paste 28 is thus placed in fluid communication with the nozzle 26. Still further, forward displacement of the plunger 18 will cause the paste 28 to travel through the nozzle 26 before finally being dispensed.

In FIGS. 6 to 9 there is shown a further embodiment of container in accordance with the present invention. This embodiment of the present invention has similarities with the embodiment of FIGS. 1 to 5 and like reference numerals denote like parts.

In FIGS. 6 to 9 there is shown a container 60 in which the internal surface 11 of the body 12 has an internal step 62 such that the proximal end 13a of the body 12 is of larger dimension than the distal end.

Further, the side wall 37 of the receptacle is provided with an open sided annular recess 64 adjacent inner wall 36.

Figure 8:
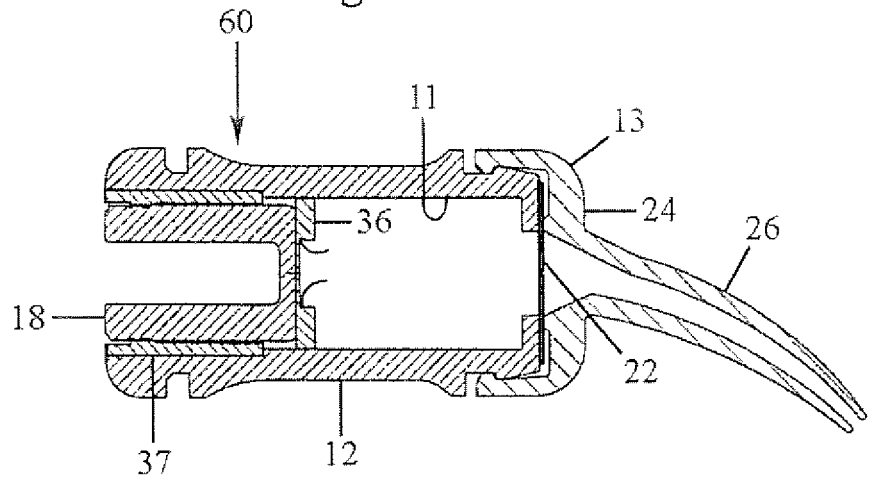
FIG. 8 is a longitudinal sectional view of the container of FIG. 6 in a further partially activated condition.
Figure 9:
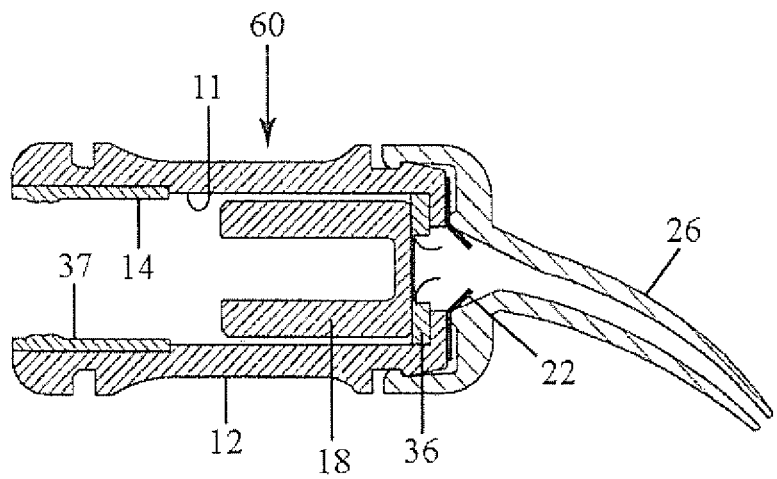
FIG. 9 is a longitudinal sectional view of the container of FIG. 6 in a fully activated condition.

As can be seen the arrangement of the recess 64 and the step 62 enables the receptacle 14 to have a thin section 66 adjacent the inner wall 36. Thus, when force is applied to the plunger 18 as described hereinabove, the inner wall 36 breaks free of the receptacle 14 as shown in FIG. 8 at the thin section 66. This is because the section 66 is relatively weak compared to the inner wall 36. Also, because the distal end 13 of the chamber 17 is smaller in internal diameter than the proximal end portion 13a, all of the force applied to the plunger 18 is concentrated at the step 62 and the thin section 66. Thus, the inner wall 36 breaks away as described above, in use.

In other respects the container of FIGS. 6 to 9 operates in essentially the same manner as the container of FIGS. 1 to 5.

Modifications and variations as would be apparent to a skilled addressee are deemed to be within the scope of the present invention.

The invention claimed is:

1. A dental container for mixing and dispensing dental material, said container comprising a hollow body having a proximal end, a distal end and a main chamber for containing dental powder material therein; a dispensing nozzle attached to said body at said distal end; a frangible membrane located adjacent said dispensing nozzle and said distal end for forming a seal for retaining said powder in said main chamber; a liquid receptacle located within said body between said main chamber and said proximal end of said body, said liquid receptacle having a side wall and an inner end wall for sealing said liquid receptacle, said inner end wall having, a central weakened portion; a plunger at said proximal end of said body in engagement with said liquid receptacle and movable axially inwardly of said body for creating hydraulic pressure on said liquid receptacle and causing said central weakened portion to break so that liquid within said liquid receptacle enters said main chamber and mixes with powder contained therein for forming a paste; continued axial movement of said plunger creates pressure on said inner wall causing it to break away from said side wall; said plunger and said inner end wall being further movable toward said distal end for creating hydraulic pressure by means of said paste fox causing said frangible membrane to burst and allowing said paste to flow outwardly through said dispensing nozzle.

2. A dental container according to claim 1 including an end cap mounted on said distal end of said body, said end cap having an aperture in alignment with said frangible membrane, and said dispensing nozzle being connected to said end cap.

3. A dental container according to claim 1 wherein said liquid receptacle includes an outwardly facing open end and a closed inner end, said plunger being mounted in said open end of said liquid receptacle.

4. A dental container according to claim 1 wherein said side wall of said liquid receptacle has a weakened region adjacent to said inner wall defining a break point such that a minor front portion of said side wall remains attached to said inner end wall when it breaks away from said liquid receptacle.

5. A dental container according to claim 1 wherein said inner end wall of said liquid receptacle includes a sharp substantially right angled bend with said side wall devoid of any radius such that said inner end wall breaks entirely away from said side wall under said by pressure created by said plunger.

6. A dental container according to claim 1 wherein said body at said proximal end includes an inwardly, facing recess arranged to be engaged with an outwardly facing projection on said liquid receptacle for holding said side wall of said liquid receptacle fixed within said body during movement of said plunger.

7. A dental container according to claim 1 wherein said main chamber includes an annular step internally thereof, said liquid receptacle having an annular recess adjacent said inner end wall to provide said liquid receptacle with a thin section adjacent said inner end wall, said annular recess being in initial engagement with said annular step whereby said inner end wall of said liquid receptacle breaks away from said side wall at said thin section under said pressure from said plunger.

* * * * *